United States Patent [19]

Bindra et al.

[11] Patent Number: 4,479,852
[45] Date of Patent: Oct. 30, 1984

[54] METHOD FOR DETERMINATION OF CONCENTRATION OF ORGANIC ADDITIVE IN PLATING BATH

[75] Inventors: Perminder S. Bindra, Ossining; Allan P. David; Raymond T. Galasco, both of Binghamton; David N. Light, Putnam Valley, all of N.Y.

[73] Assignee: International Business Machines Corporation, Armonk, N.Y.

[21] Appl. No.: 459,930

[22] Filed: Jan. 21, 1983

[51] Int. Cl.³ .............................................. G01N 27/46
[52] U.S. Cl. ...................................... 204/1 T; 204/434
[58] Field of Search ............... 204/1 T, 1 K, 231, 433, 204/434

[56] References Cited

U.S. PATENT DOCUMENTS

| | | | |
|---|---|---|---|
| 3,925,168 | 12/1975 | Costas | 204/1 T |
| 4,132,605 | 1/1979 | Tench et al. | 204/434 X |
| 4,146,437 | 3/1979 | O'Keefe | 204/434 X |
| 4,217,189 | 8/1980 | Kerby | 204/1 T X |
| 4,324,621 | 4/1982 | Kerby | 204/1 T |

OTHER PUBLICATIONS

Koretzky, "Increasing the Deposition Rate of Electroless Solutions", IBM Technical Disclosure Bulletin, vol. 9, No. 11, 4/67, p. 1634.

F. Mansfeld, "The Copper Plating Bath Monitor", Plating and Surface Finishing, May 1978, pp. 60–62.

M. Panmovic, "An Electrochemical Control System for Electroless Plating Bath", Journal Electrochem. Soc., Feb. 1980, pp. 365–369.

Primary Examiner—G. L. Kaplan
Assistant Examiner—Nam X. Nguyen
Attorney, Agent, or Firm—Pollock, Vande Sande & Priddy

[57] ABSTRACT

The concentration of an organic additive in a plating bath is determined by providing a polished and constant current density preplated rotating disc cathode, a reference electrode and anode in an electrolytic copper plating bath, passing an electric current from the anode to the cathode and reference electrode; measuring the voltage difference between the cathode and reference electrode; and comparing the difference to values for known concentrations of the organic additive.

22 Claims, 3 Drawing Figures

METHOD FOR DETERMINATION OF CONCENTRATION OF ORGANIC ADDITIVE IN PLATING BATH

DESCRIPTION

1. Technical Field

The present invention is concerned with a method for determining the concentration of organic additives in plating baths and particularly in acidic electrolytic copper plating baths. The present invention is preferably concerned with a galvanostatic step technique for determining the concentration of organic additives in acidic electrolytic copper plating baths. The present invention is concerned with single or multicomponent organic addition system for acidic electrolytic copper plating baths.

2. Background Art

One technique used extensively for plating copper onto a substrate is by electrolytic process using, for example, an acidic copper bath. Acidic copper baths generally contain at least one organic addition agent.

The organic addition agent is the main ingredient which affects the performance of acidic copper electrolytic baths. The organic addition agent is the primary constituent for improving leveling and throwing power. Throwing power refers to the ability to provide uniform plating in through holes for interconnections as well as on the top surface of multilayer printed circuit boards.

The organic additive is crucial in defining optimal plated metallurgy. For instance, the organic additives greatly influence such properties as ductility, tensile strength, and solderability.

In a manufacturing environment, the addition agent is constantly replenished in acid copper baths according to a predetermined amp-hour schedule. The Hull cell is utilized as a visual aid to determine if bright copper plating occurs. However, no completely satisfactory proven technique from a commercial viewpoint for monitoring the concentration of addition agent in the bath is presently available. In fact, the lack of a concentration monitor for organic addition agents which satisfies the requirements for use in a manufacturing environment is a major limitation of electrolytic acidic copper plating. Monitoring the concentration of an organic additive in the plating bath is greatly complicated by the presence of contaminants such as residues from photoresists and solvents used in circuit development, as well as airborne impurities and substances leached from plating tanks and cell components. Furthermore, the concentration of the additive itself drifts unpredictably with time as the additive is incorporated in the deposit, reduced at the cathode, oxidized at the anode, and reacted with other constituents of the bath.

Various techniques have been suggested for monitoring certain components in electroplating baths. For instance, U.S. Pat. No. 3,925,168 to Costas suggests a method of determining the concentration of "roughening" agents, such as glue, in an acidic copper plating bath by immersing a test cathode and a reference electrode in a plating bath, maintaining either the voltage difference between the electrodes or the current density constant, measuring whichever of current density or voltage difference which is not held constant, and comparing the resulting data with that for known concentrations of roughening agents.

U.S. Pat. No. 4,132,605 to Tench, et al. suggests a method for determining the concentration of an organic leveling agent in a bath for electroplating metals such as copper. In the method of Tench, et al., metal is plated, then stripped from a surface, the coulombs used during the plating and stripping cycle are measured, and the data obtained are correlated with that for baths having a known concentration of additives.

U.S. Pat. No. 4,146,437 to O'Keefe suggests a method for determining whether an electrolytic solution is suitable for use in an electroplating process. In accordance with this method, electrodes are placed in the solution, voltage is applied to the electrodes to plate metal onto the cathode, the voltage is then reversed to redissolve the plated metal, the current is recorded as a function of voltage, and the performance characteristics of the plating solution is compared to that of known plating solutions. O'Keefe suggests preparing the cathode by polishing with 600 grit Carbimet paper before use (column 9, lines 67 and 68).

U.S. Pat. No. 4,217,189 to Kerby suggests a method for controlling the plating of zinc in an electro-winning process. In this method the purity of the electrolyte is determined by measuring the activation over-potential between a cathode and a reference electrode in a test cell containing the plating solution and relating the activation overpotential to the concentrations of impurities in the sample.

U.S. Pat. No. 4,324,621 to Kerby suggests a method of controlling the electrodeposition of metals by measuring the activation over-potential between a cathode and a reference electrode at the potential at which deposition of metal has just begun. The concentration of additives affecting polarization are said to be determined by this method. Kerby suggests using "smooth" surfaces for the cathodes (column 6, lines 4 to 11).

SUMMARY OF INVENTION

The present invention provides an electrochemical technique for monitoring the concentration of organic additives in electrolytic copper plating baths. The present invention makes it possible to accurately monitor the organic additives and, therefore, to precisely control the plating process by maintaining the concentration of organic additives within specified limits.

In particular, the present invention provides a method for determining the concentration of at least one organic additive in an acidic electrolytic copper plating bath. The method of the present invention comprises preparing a cathode by electroplating a copper film onto a substrate by immersing the substrate in a copper plating bath and plating copper thereon at a constant current density and constant voltage. The cathode, as prepared above, a reference electrode, and an anode are all incorporated into an acidic electrolytic copper plating bath. An electric current at a constant current density is passed from the anode to the cathode and reference electrode. The voltage difference between the cathode and reference electrode is measured. The concentration of the at least one organic additive is determined by comparing the voltage difference to values obtained for known concentrations of the at least one organic additive.

BEST AND VARIOUS MODES FOR CARRYING OUT INVENTION

Figure 1:
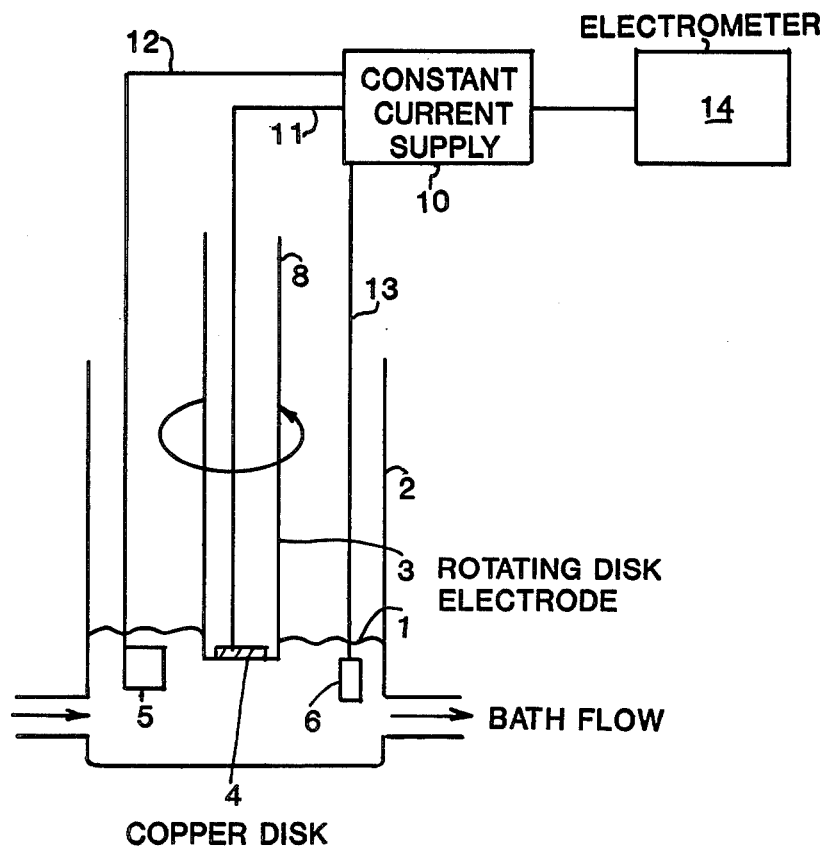
FIG. 1 is a schematic diagram of a monitoring apparatus suitable for carrying out the process of the present invention.

The present invention is concerned with determining the concentration of at least one organic additive in an acidic electrolytic copper plating bath. The organic additive can be a single component or multicomponent additive. If a multicomponent additive is employed, the calibration curve is obtained by providing different quantities of the multicomponent additive wherein the relative amounts of each of the components remains the same. It is assumed, in such instance, that during the actual plating, the relative amounts of the different components in a multicomponent organic additive composition remain substantially the same. In fact, multicomponent compositions for such purpose are preselected so that the relative amounts with respect to each other do remain substantially the same throughout the plating process. The preferred organic additives monitored, according to the process of the present invention, are the polyalkylene glycols and, most preferably, polyethylene glycol and polypropylene glycol. The preferred polyethylene glycols and polypropylene glycols usually have molecular weights of about 400 to about 1,000 and preferably about 600 to about 700.

When employing a multicomponent organic additive, such preferably contains a polyalkylene glycol along with a sulfur containing compound such as a benzene sulfonic acid, safranine-type dyes, and sulforganic aliphatic compounds including disulfides, and/or a nitrogen containing compound such as an amide. Examples of contemplated amides include acrylamide and propylamide.

The plating bath is an acidic electrolytic copper plating bath and includes a source of cupric ions and an inorganic mineral acid such as sulphuric acid. The preferred source of the cupric ions is $CuSO_4$. In addition, it is preferred that the plating bath include a source of chloride ions which preferably is from HCl. Preferred copper plating baths contain the source of cupric ions in an amount of about 0.1 to about 0.3 molar, the inorganic acid in amounts of about 1.5 to about 2.5 molar, the chloride ions in amounts of about 30 to about 70 ppm, and about 0.5 to about 1.25% by volume of the organic additive.

In accordance with the present invention, it is essential in obtaining sensitive and reliable measurements, to preplate the cathode prior to the actual plating process. In particular, the cathode is preplated by electroplating a copper film onto a suitable substrate such as a copper, gold, or carbon substrate by immersing the substrate in a copper plating bath and plating copper thereon at a substantially constant current density and substantially constant voltage. In the preplating, the amount of organic additive is either zero or is maintained at a constant value during the preplating. The preplating is continued until a copper film of about the same smoothness of that of the copper to be subsequently plated, which is usually until about 0.5 to about 1.5 microns form on the substrate. With constant current densities in the range of about 1 to about 12 $mA/cm^2$, this usually takes about 3 to 7 minutes. In addition, the cathode, according to the preferred aspects of the present invention, is polished prior to the preplating in order to provide as smooth a coating as possible. The polishing can be carried out on a polish wheel employing an alumina abrasive of about 0.3 microns for about 30 seconds to about 1 minute.

After the cathode is preplated, the cathode, a reference electrode, and an anode are provided in the acidic electrolytic copper plating bath containing the organic additive. Suitable reference electrodes are mercury-mercurous sulfate electrodes and $Cu^{+2}$/copper electrodes.

The anode surface is generally copper, a noble metal such as gold, or carbon.

The anode surface area is usually at least about 5 times the surface area of the cathode.

The plating is carried out under constant current density. The current density is usually in the range of about 1 $mA/cm^2$ to about 12 $mA/cm^2$ and preferably about 8 $mA/cm^2$ to about 12 $mA/cm^2$. The electric current is passed from the anode to the cathode and reference electrode and the voltage difference between the cathode and the reference electrode is measured. The potential for plating with reference to standard calomel electrodes is about 0.4 to 0.5 volts.

Since the voltage difference relates to a difference in the concentration of the organic additive, a comparison of the measured voltage difference to voltage difference values previously determined for known concentrations of the particular organic additive shows concentration of organic additive in the plating bath. This can be constantly monitored so when the value drops below a particular preselected or predetermined amount, then additional organic additive can be incorporated into the bath to bring the amount to the desired value.

Along these lines, it is noted that, in the absence of organic additives, the rest potential of the electrode, $E_0$, represents a condition where the rates of copper reduction and oxidation are equal. When a current is imposed during electroplating, the cathode potential is polarized to a more negative value, $E_1$. The overpotential, $\eta$, is defined as the potential difference $E_1$ minus $E_0$.

This overpotential represents a relative measurement of the additional energy input required for plating copper at a given rate. With placement of organic addition agents in a bath, plating at a given rate, the cathode potential is polarized to a new value, $E_2$, and a new overpotential $E_2$ minus $E_0$. This change in cathode potential and overpotential is caused by different energy requirements at one or more stages of the copper deposition reaction sequence.

Reference to FIG. 1 illustrates suitable apparatus for carrying out the process of the present invention. Numeral 1 refers to the depth of the plating bath in the plating tank 2. Numeral 3 refers to a rotating disk electrode having a copper disk 4 where the plating occurs and Teflon ® jacket 8. The copper disk is connected to the constant current supply source 10 by wire 11. The anode 5 is electrically connected to the constant current supply source 10 via wire 12. The reference electrode 6 is connected to the constant current supply source 10 by wire 13. The voltage differences are measured by the electrometer 14.

The following nonlimiting examples are provided to further illustrate the present invention.

EXAMPLE 1

A gold rotating disk cathode, having a surface area of about 0.442 $cm^2$ is polished on a polish wheel for about 1 minute with alumina abrasive of about 0.3 microns, then the polished cathode is preplated in a copper electrolytic bath containing about 0.267M $CuSO_4$, about 1.67M $H_2SO_4$, and about 50 ppm $Cl^-$ for about 5 minutes. The preplated cathode, along with a gold anode having a surface area about 5 times that of the cathode, and a $Cu^{+2}/Cu$ reference electrode are maintained in a plating bath containing about 0.267M $CuSO_4$, 1.67M $H_2SO_4$, and 50 ppm $Cl^-$ diluted to 40% with water for enhanced sensitivity.

The bath is maintained oxygen-free by constantly bubbling pure nitrogen through it. The current density is about 11.3 mA/cm$^2$. Varying amounts of a polyethylene glycol containing additive are added to the solution and the cathode potential is recorded at equilibrium (e.g., about 5 minutes after the current step occurs). Each amount is tested five times to establish reproducibility. Analysis of the data indicates that the measured potentials at each additive concentration are statistically different. The potential versus the known amount of additive can be slotted to provide a standard curve which can be used to determine unknown quantities of the same additive.

Figure 2:
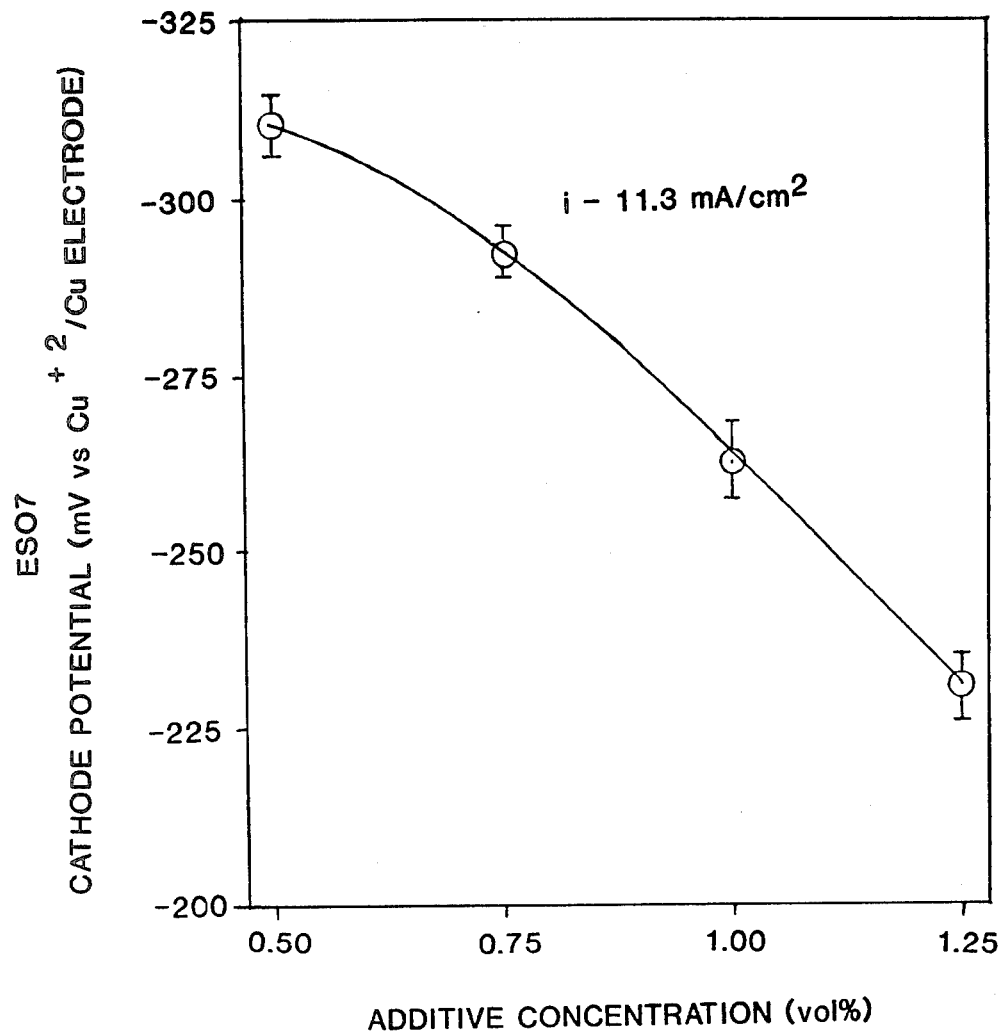
FIGS. 2 and 3 represent calibration curves for an organic additive using different plating conditions.

FIG. 2 is a representative curve of concentration of the polyethylene glycol containing organic additive versus potential.

EXAMPLE 2

Figure 3:
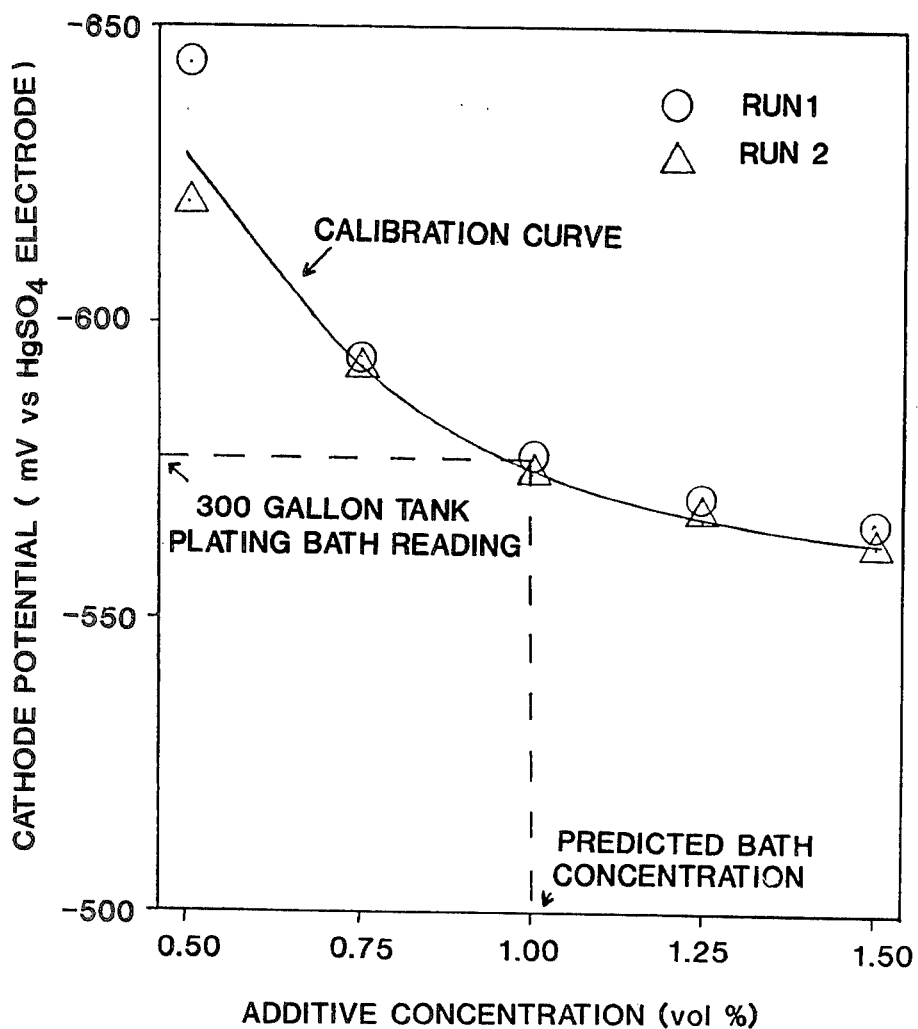

Measurements are made with a 5.1 cm$^2$ stationary copper cathode preplated as discussed in Example 1, a 10 cm$^2$ copper anode, and a mercury-mercurous sulfate reference electrode. A magnetic stirrer provides solution agitation. The current density is maintained at 10 mA/cm$^2$. The plating solution consists of 0.267M $CuSO_4$, 1.67M $H_2SO_4$, and 50 ppm $Cl^-$ with a different known amount of polyethylene glycol containing organic additive for each test. The results of two separate experiments are shown in FIG. 3. The cathode potential for a sample obtained from a working 300 gallon plating tank is also presented. The predicted additive concentration for this sample is 1.0 volume % which is the nominal operating bath value.

What is claimed is:

1. A method of determining the concentration of at least one organic additive in an acidic electrolytic copper plating bath comprising the steps of:
    (a) preparing a cathode by electroplating a copper film onto a substrate by immersing the substrate in a copper plating bath and preplating copper thereon at a constant current density and constant voltage; said cathode being a rotating disk electrode;
    (b) providing in an acidic electrolytic copper plating bath, said cathode from step (a), a reference electrode, and an anode;
    (c) passing an electric current at a constant current density from said anode to said cathode;
    (d) measuring the voltage difference between said cathode and said reference electrode; and
    (e) comparing the measured voltage difference from step (d) with previous measured values for known concentrations of said organic additive.

2. The method of claim 1 whereby the smoothness of the coating from the preplating is the same as that of the copper plated during the measuring step.

3. The method of claim 1 wherein the thickness of the copper from the preplating is about 0.5 to about 1.5 microns.

4. The method of claim 1 wherein the preplating is carried out for about 3 to about 7 minutes.

5. The method of claim 1 wherein the preplating and plating are carried out at a substantially constant current density of about 1 mA/cm$^2$ to about 12 mA/cm$^2$.

6. The method of claim 1 wherein the preplating and plating are carried out at a substantially constant current density of about 8 mA/cm$^2$ to about 12 mA/cm$^2$.

7. The method of claim 1 wherein said organic additive contains at least one polyalkylene glycol.

8. The method of claim 7 wherein said polyalkylene glycol is polyethylene glycol or polypropylene glycol.

9. The method of claim 7 wherein said polyalkylene glycol is polyethylene glycol.

10. The method of claim 1 wherein said plating bath contains a source of cupric ions and an inorganic acid.

11. The method of claim 10 wherein said plating bath contains $Cl^-$ ions.

12. The method of claim 10 wherein said bath contains about 0.1 to 0.3 M of said source of cupric ions and about 1.5 to about 2.5 M of said acid.

13. The method of claim 12 wherein said source of copper is $CuSO_4$, and said acid is $H_2SO_4$, the amount of said $Cl^-$ is about 30 to 70 ppm.

14. The method of claim 13 further includes maintaining the amount of organic additive with a predetermined value of about 0.5 to about 1.25% by volume.

15. The method of claim wherein said value is about 1% by volume.

16. The method of claim 15 wherein the amount of said $CuSO_4$ is about 0.267 M, the amount of said $H_2SO_4$ is about 1.67 M, and the amount of said $Cl^-$ is about 50 ppm.

17. The method of claim 10 wherein said source of copper is $CuSO_4$ and said acid is $H_2S_4$.

18. The method of claim 1 wherein said cathode is polished prior to the preplating.

19. The method of claim 1 wherein the plating bath is diluted with water for enhanced sensitivity.

20. The method of claim 19 wherein the plating bath is diluted to 40% with water.

21. The method of claim 1 wherein said cathode is a noble metal.

22. The method of claim 1 wherein said cathode is gold.

* * * * *

UNITED STATES PATENT AND TRADEMARK OFFICE
CERTIFICATE OF CORRECTION

PATENT NO. : 4,479,852

DATED : October 30, 1984

INVENTOR(S) : Bindra, et al.

It is certified that error appears in the above-identified patent and that said Letters Patent is hereby corrected as shown below:

Column 6, line 46, Claim 17, please delete "$H_2S_4$" and insert therefor --- $H_2SO_4$ ---.

Signed and Sealed this

Seventh Day of May 1985

[SEAL]

Attest:

DONALD J. QUIGG

Attesting Officer — Acting Commissioner of Patents and Trademarks